United States Patent [19]

Nishizawa et al.

[11] Patent Number: 4,634,514

[45] Date of Patent: Jan. 6, 1987

[54] ELECTROCHEMICAL APPARATUS AND METHOD OF MANUFACTURING THE SAME

[75] Inventors: Hitoshi Nishizawa; Kazuyoshi Shibata, both of Nagoya, Japan

[73] Assignee: NGK Insulators, Ltd., Japan

[21] Appl. No.: 827,107

[22] Filed: Feb. 7, 1986

[30] Foreign Application Priority Data

Feb. 14, 1985 [JP] Japan .................................. 60-26808
Feb. 23, 1985 [JP] Japan .............................. 60-24181[U]
Feb. 23, 1985 [JP] Japan .............................. 60-24182[U]

[51] Int. Cl.$^4$ .......................................... G01N 27/58
[52] U.S. Cl. ................... 204/406; 29/592 R; 204/412; 204/425
[58] Field of Search ............... 204/406, 425, 1 S, 412; 29/592 R

[56] References Cited

U.S. PATENT DOCUMENTS

| | | | |
|---|---|---|---|
| 3,616,274 | 10/1971 | Eddy | 204/1 T |
| 4,272,329 | 6/1981 | Hetrick | 204/1 T |
| 4,272,330 | 6/1981 | Hetrick | 204/1 T |
| 4,472,247 | 9/1984 | Rohr et al. | 204/1 T |
| 4,505,807 | 3/1985 | Yamada | 204/425 |

FOREIGN PATENT DOCUMENTS

| | | | |
|---|---|---|---|
| 0066851 | 12/1982 | European Pat. Off. | 204/1 T |
| 0067326 | 12/1982 | European Pat. Off. | 204/1 T |
| 0121905 | 10/1984 | European Pat. Off. | 204/1 T |
| 0148622 | 7/1985 | European Pat. Off. | 204/1 T |

Primary Examiner—G. L. Kaplan
Attorney, Agent, or Firm—Parkhurst & Oliff

[57] ABSTRACT

In an electrochemical apparatus utilizing an electrochemical cell having a solid-electrolyte and at least one pair of porous electrodes arranged in contact with the solid-electrolyte, wherein one electrode of the pair of electrodes is exposed through a diffusion means having a diffusion resistance with respect to a gas to be measured in a space in which the gas to be measured is present, and an atmosphere near one of the electrodes is controlled by an electrode reaction due to a current flowing through the pair of electrodes, a first branch conductor and a second branch conductor are formed by dividing one of conductors respectively connected to the electrodes, and at least one adjustable first resistive means and at least one second resistive means are respectively formed in the first branch conductor and the second branch conductor. Therefore, a predetermined current flows through either the first or second resistive means, and thus it is possible to obtain the electrochemical apparatus which maintains a constant quality in large scale manufacturing.

14 Claims, 16 Drawing Figures

FIG_4
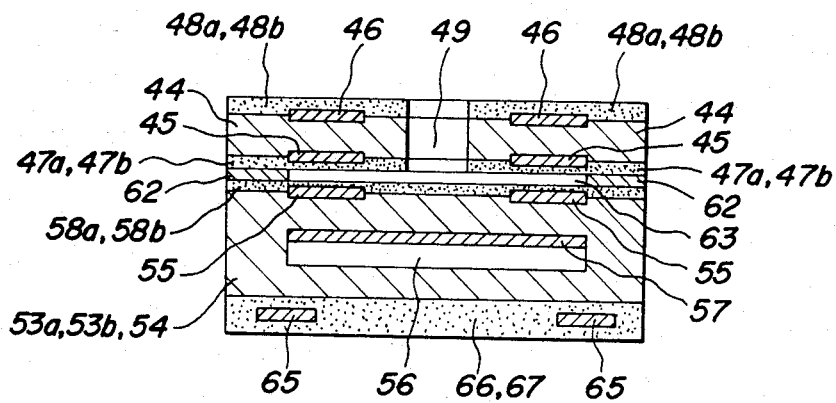
FIG_5
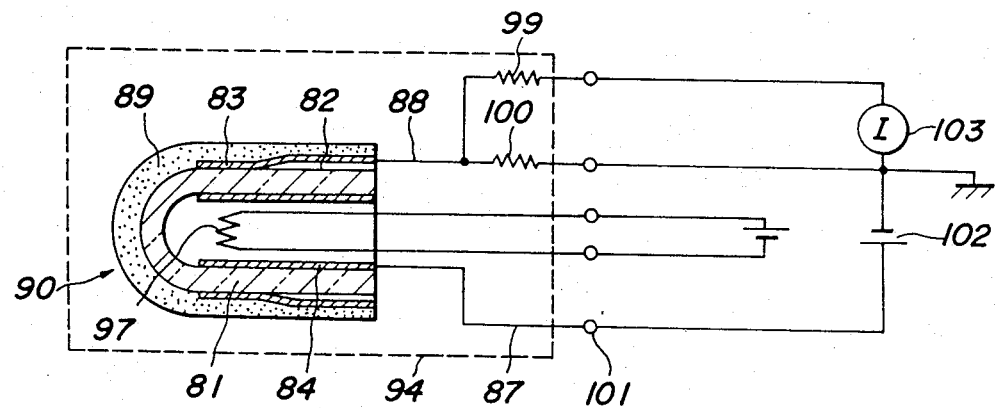

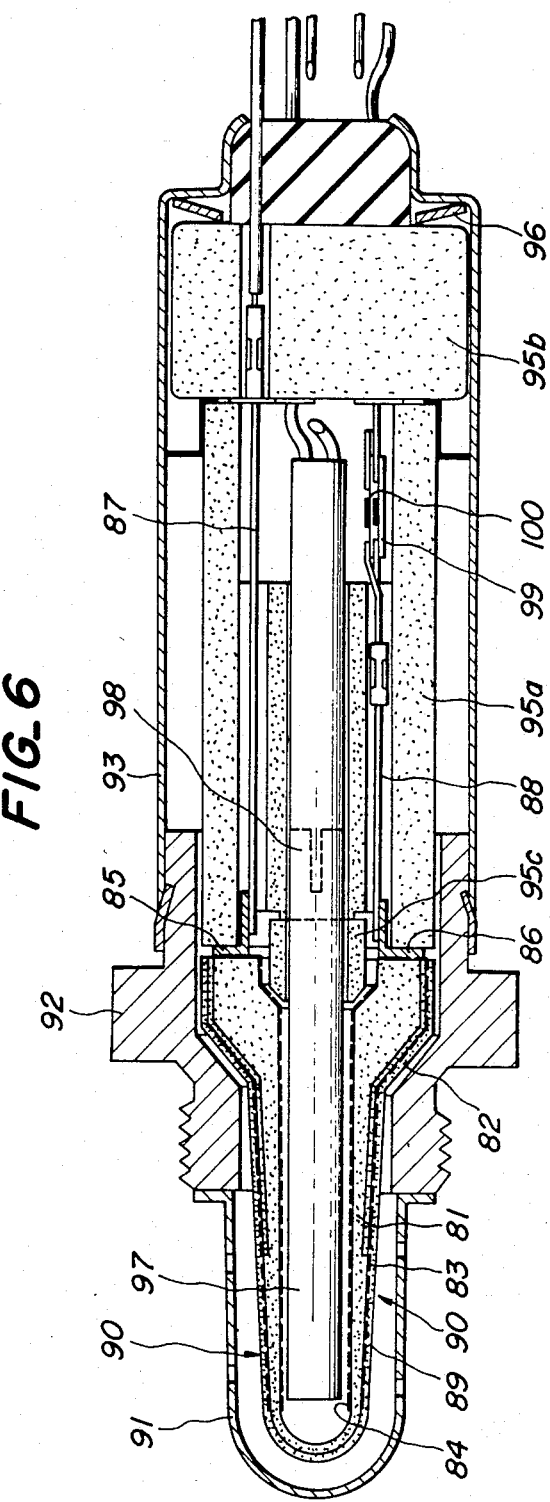
FIG_6

FIG_7
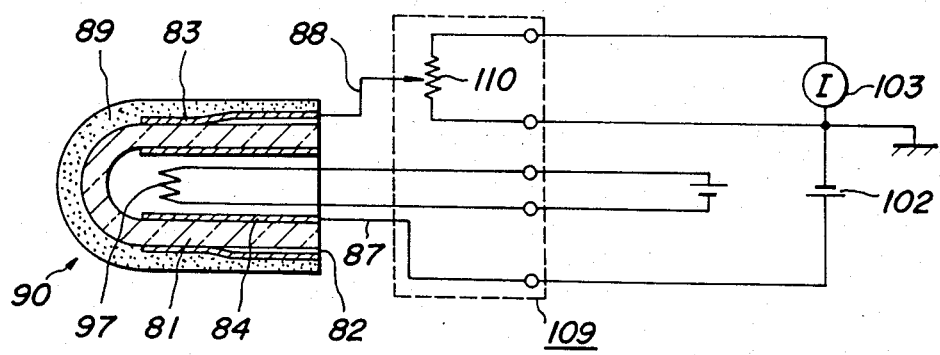

FIG_11
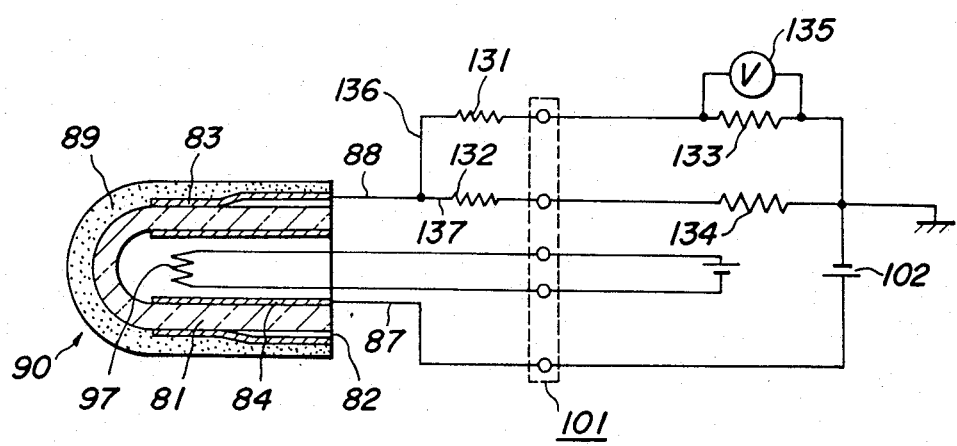
FIG_12
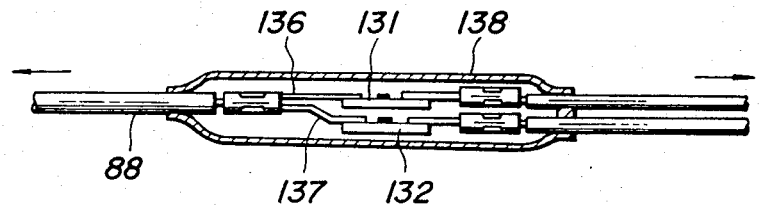

FIG_14A
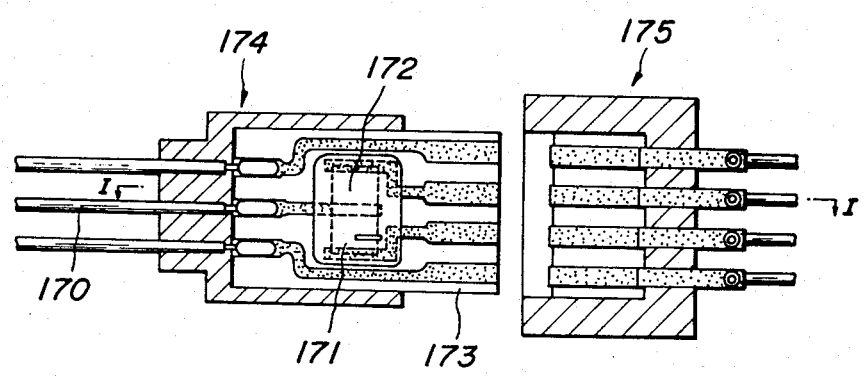
FIG_14B
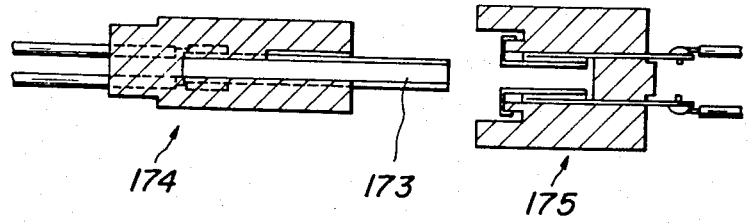

ELECTROCHEMICAL APPARATUS AND METHOD OF MANUFACTURING THE SAME

BACKGROUND OF THE INVENTION

1. Field of the Invention

The present invention relates to an electrochemical apparatus which detects a gas concentration by using a solid-electrolyte and a method of manufacturing the above electrochemical apparatus, and more particularly relates to an electrochemical apparatus which has small variation in output signals therebetween with respect to the same gas to be measured.

2. Related Art Statement

Heretofore, as an apparatus comprising an electrochemical cell using the solid-electrolyte such as an oxygen sensor which detects an oxygen concentration in an exhaust gas from an internal combustion engine, there has been known a sensor wherein an electrochemical cell is constructed from a zirconia porcelain as the solid-electrolyte having an oxygen ion-conductivity and a pair of porous electrodes, and an electrochemical pumping is effected by flowing a current through a pair of porous electrodes, while one of the porous electrodes is brought into contact with an outer gas to be measured through a gap having a gas diffusion resistance or a diffusion means such as porous ceramics etc., and a pumping current corresponding to the outer oxygen concentration is outputted. Further, there has been known a detector (electrochemical apparatus) for detecting a hydrogen gas, a carbonic acid gas, etc., by utilizing an electrochemical pumping and a gas diffusion theory, as is the same as the oxygen sensor mentioned above.

However, when large scale manufacturing is performed for the known electrochemical apparatus, there is a drawback that diffusion resistances of the diffusion means in the electrochemical cells are largely varied, respectively, so that the outputs of respective apparatus are not constant with respect to the same gas to be measured, i.e. it is difficult to obtain the electrochemical apparatus. With constant quality.

Further, as for the diffusion means having a diffusion resistance with respect to a gas to be measured, use is made of a plain gap or a pin-hole brought into contact with the outer gas to be measured and surrounded by a ceramic body such as the solid-electrolyte, or a porous ceramic layer formed by a flame spraying, or a burning after screen printing or laminating. In this case, since the diffusion resistances between respective electrochemical cells largely vary corresponding to the conditions such as a dimension of the solid-electrolyte ceramic body, a thickness of the gap in laminating, amounts of warp and a deformation in burning and the flame spraying condition, it is also difficult to obtain the electrochemical apparatus with constant quality.

SUMMARY OF THE INVENTION

The present invention has for its object to eliminate the drawbacks mentioned above and to provide an electrochemical apparatus which maintains a constant quality in a large scale manufacturing.

According to the invention, an electrochemical apparatus utilizing an electrochemical cell having a solid-electrolyte and at least one pair of porous electrodes arranged in contact with said solid-electrolyte, wherein one of said pair of electrodes is exposed through a diffusion means having a diffusion resistance with respect to a gas to be measured in a space in which the gas to be measured is present and an atmosphere near said one of the electrodes is controlled by an electrode reaction due to a current flowing through said one pair of electrodes, comprises a first branch conductor and a second branch conductor formed by dividing one of conductors respectively connected to said electrodes and arranged connectably to an external power source;

at least one first resistive means formed in said first branch conductor, a resistive value of which can be arbitrarily adjusted; and at least one second resistive means formed in said second branch conductor; whereby a predetermined current corresponding to a predetermined concentration of the gas to be measured flows through one of said first or second resistive means.

Another object of the invention is to provide a method of manufacturing the above electrochemical apparatus.

According to the invention, a method of manufacturing an electrochemical apparatus utilizing an electrochemical cell having a solid-electrolyte and at least one pair of porous electrodes arranged in contact with said solid-electrolyte, wherein one of said pair of electrodes is exposed through a diffusion means having a diffusion resistance with respect to a gas to be measured in a space in which the gas to be measured is present, and an atmosphere near said one of the electrodes is controlled by an electrode reaction due to a current flowing through said one pair of electrodes, comprises the steps of forming a first branch conductor and a second branch conductor by dividing one of conductors respectively connected to said electrodes;

forming at least one first resistive means in said first branch conductor, a resistance of which can be arbitrarily adjusted;

forming at least one second resistive means in said second branch conductor; and adjusting the resistance of said first resistive means so as to obtain a predetermined output in response to a predetermined component concentration of the gas to be measured from a current through one of said first branch conductor and second branch conductor.

Still another object of the invention is to provide an electrochemical apparatus which can adjust an output thereof easily.

According to the invention, an electrochemical apparatus including a connector portion for use in a connection with an external power source and an electrochemical cell having a solid-electrolyte and at least one pair of porous electrodes arranged in contact with said solid-electrolyte, wherein one of said pair of electrodes is exposed through a diffusion means having a diffusion resistance with respect to a gas to be measured to a space in which the gas to be measured is present, and an atmosphere near said one of the electrodes is controlled by an electrode reaction due to a current flowing through said one pair of electrodes, comprises:

a first branch conductor and a second branch conductor formed by dividing one of conductors respectively connected to said electrodes and arranged connectably to the external power source through said connector portion;

at least one first resistive means arranged between said electrochemical cell and said connector portion, a resistance of which can be arbitrarily adjusted; and at least one second resistive means formed in said second branch conductor; whereby a predetermined current corresponding to a predetermined concentration of the gas to be measured flows through one of said first or second resistive means.

BRIEF DESCRIPTION OF THE DRAWINGS

FIG. 4 is a cross sectional view depicting an embodiment cut along the line V—V in FIG. 3;

FIG. 5 is a schematic view showing one embodiment of the electrochemical apparatus according to the invention together with the external circuit;

FIG. 6 is a partial cross sectional view illustrating one embodiment of a sensor formed by arranging the electrochemical cell shown in FIG. 5 in a protector;

FIG. 7 is a schematic view showing another embodiment of the electrochemical apparatus according to the invention together with the external circuit;

FIG. 11 is a schematic view depicting still another embodiment of the electrochemical apparatus according to the invention together with the external circuit;

FIG. 12 is a schematic view illustrating one embodiment of the resistor and the branch line of the embodiment shown in FIG. 11;

FIG. 14A is a partial cross sectional view showing the connector portion of the embodiment shown in FIG. 13, and FIG. 14B is a partial cross sectional view cut long I—I line of the embodiment shown in FIG. 14A.

DESCRIPTION OF THE PREFERRED EMBODIMENTS

At first, a concept of the present invention will be explained briefly.

In the present invention, it is assumed that a pumping current i.e. a current, flowing between a pair of electrodes which is usually used as an output signal, is inevitably varied due to a variation of a diffusion resistance of a diffusion means in an electrochemical cell, and the following measures are performed instead of using the pumping current directly as the output signal.

Figure 1:
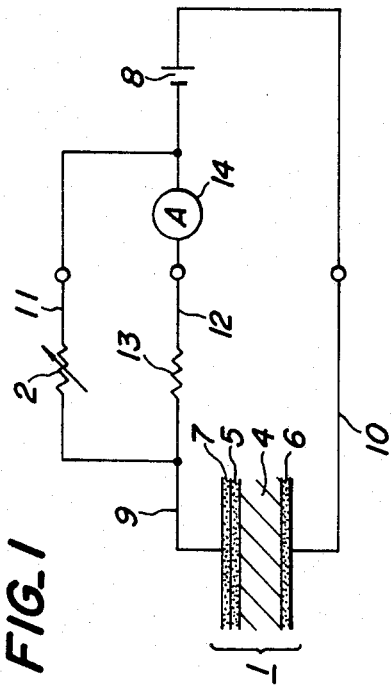
FIG. 1 is a circuit diagram for explaining a method of adjusting an output of the electrochemical apparatus according to the invention.

That is to say, as shown in FIG. 1, use is made of a pair of parallel resistors 2 and 13 connected in series with an electrochemical cell 1 so as to divide the pumping current, and the thus divided current is detected by an ammeter 14 as the output signal. Then, the apparatus mentioned above is operated in a predetermined atmosphere (standard gas) having a predetermined concentration of a component to be measured, and resistance of the resistor 2 is adjusted respectively one by one to make the output signal equal to a predetermined value corresponding to the atmosphere. Therefore, it is necessary to construct the resistor 2 as a resistive means which can vary its resistance at will (hereinafter, abbreviated as variable resistor).

In this embodiment shown in FIG. 1, the electrochemical cell 1 comprises a solid-electrolyte 4, a pair of porous electrodes 5, 6 and a diffusion means 7, and to a pair of the electrodes 5, 6 are respectively connected conductors 9, 10 for introducing a current from an external D.C. power source 8. Then, the resistors 2, 13 are respectively arranged in branch conductors 11, 12 of the conductor 9.

In this manner, the pumping current is divided by a pair of the resistors 2 and 13 into the current through the resistor 2 and the current through the resistor 13, the latter is the output signal. The output signal thus obtained becomes proportional to the pumping current. Moreover, since use is made of the variable resistor 2 to adjust easily the output signal, it is possible to obtain electrochemical apparatus each having constant quality in large scale manufacturing.

In the present invention, as for the solid-electrolyte having an ion-conductivity for use in the electrochemical cell, use is made of a zirconia porcelain having an oxygen ion-conductivity, a solid solution of $Bi_2O_3$—$Y_2O_3$ system, $SrCe_{0.95}Yb_{0.05}O_{3-\alpha}$ having a proton conductivity, $CaF_2$ having a halogen ion-conductivity. Moreover, a shape of this solid-electrolyte is not limited at all, and it is possible to use a plate-like shape or a standard cylindrical shape having a bottom.

Further, the electrochemical cell according to the invention comprises at least the solid-electrolyte mentioned above, a pair of the porous electrodes arranged in contact with the solid-electrolyte and the diffusion means arranged between one of the electrodes and the gas to be measured, and a concentration of the component in the gas to be measured is detected on the basis of an ion pumping function due to a current flowing between these electrodes and the diffusion theory due to the diffusion in concentration of the gas component to be measured. In this manner, as to the electrochemical cell, it is necessary to use at least a pair of the porous electrodes arranged in contact with the solid-electrolyte, but it is possible to use two pair of or more than two pair of the electrodes or to use more than two solid-electrolytes. Moreover, another electro-chemical cell (sensing cell) based on the theory of concentration cell having the solid-electrolyte and a pair of the porous electrodes may be used for measuring an atmosphere near one of the porous electrodes exposed in the gas to be measured through the diffusion means, other than the electrochemical cell according to the invention for the ion pumping function. In this case, an applicable field of the electrochemical apparatus according to the invention can be widened, and thus it is preferable to use such sensing cell.

Further, the diffusion means functions to expose at least one of the porous electrodes in the external gas to be measured under a diffusion resistance, and is formed by a small space such as a pin-hole, a cavity and a gap or by a porous layer. These diffusion means mentioned above are well known as prior art.

Furthermore, it is preferable that a portion of conductors connected respectively to a pair of the electrodes and a part of a first and a second branch conductors formed by dividing one of the conductors are arranged on the solid-electrolyte. In this case, the conductors and the branch conductors are arranged on the solid-electrolyte by means of a burning operation which occurs after screening a conductive paste, and more preferably they are arranged on the solid-electrolyte through an insulation layer such as an electrical insulating ceramic so as to eliminate a leak current.

Moreover, the variable resistor connected in series with the electrochemical cell mentioned above, i.e. a first resistive means arranged in the first branch conductor which can readily adjust its resistance, varies its resistance corresponding to the pumping current of the electrochemical cell measured in the standard gas atmosphere having a predetermined concentration of the component to be measured so as to adjust the output signal of the electrochemical cell equal to the predetermined value corresponding to the concentration of the component to be measured in the standard gas. As to such a variable resistor, use may be made of various resistors which can vary their resistance such as a variable resistor element capable of adjusting its resistance, a semifixed resistor element, a thick-film resistor capable of trimming by sandblasting or using a laser and a resistor selected from a plurality of resistor elements as having a suitable resistance. Especially, the thick-film resistor preferably used for the variable resistor is formed directly on the solid-electrolyte or formed integrally on the solid-electrolyte through the insulation layer made of, for example, an electrical insulating ceramic, and is preferably arranged in a low temperature portion apart from the electrode heated by a heater or the gas to be measured with high temperature. As to a method of forming the thick-film resistor, a thick-film paste formed by mixing a ruthenium oxide powder and a glass powder with an organic binder or a thick-film paste formed by mixing a heat resisting metal powder such as platinum and platinum-rhodium and a ceramic powder such as alumina and zirconia with an organic binder is arranged on the solid-electrolyte by screen printing or is painted on a burned or un-burned solid-electrolyte substrate or on a burned or un-burned ceramic substrate such as an alumina, and then, the thus screen printed or painted substrate is burned. As to the second resistive means arranged on the second branch conductor, use is made of a resistive means having a predetermined resistance, a resistive means capable of adjusting its resistance at will as is the same as the first resistive means or a part of a resistive means having two resistive components corresponding to the first and the second resistive means such as a potentiometer.

The shape of the variable resistor as the first resistive means and the shape of the second resistive means arranged in the second branch conductor are not limited at all. However, it is preferable to form the first and second resistive means on the solid-electrolyte substrate of the electrochemical cell, because it is possible to make the construction compact in size and to protect them in an extremely easy manner by accommodating them in the protector of the electrochemical cell. Moreover, the first and the second resistive means may be formed by a sum of a plurality of resistors. Further, since the first resistive means (variable resistor) and the second resistive means used for dividing the pumping current and connected in parallel with the first resistive means are generally used in the same surrounding temperature, it is preferable that these resistive means have substantially the same temperature coefficient of resistance. In this case, since the dividing ratio of the pumping current is hardly varied in response to a variation of the temperature around these resistive means, it is possible to widen the arrangeable areas of these resistive means, so that it is advantageous if these resistive means are formed on the solid-electrolyte exposed under different temperatures in a starting state and in a stable state, respectively.

Moreover, since it is possible to compensate for the variation of the diffusion resistance generated between respective electrochemical cells by arranging at least the first resistive means (variable resistor) between the electrochemical cell and the connector portion, it is possible to obtain the electrochemical apparatus each having a constant output value i.e. a constant quality in large scale manufacturing, and thus it is not necessary to adjust the external circuit of the power source side every time the sensor is exchanged.

The present invention is not limited to the explanation mentioned above, but various modifications and alterations are possible within the scope of those skilled in the art, and it is a matter of course that the present invention includes such modifications and alterations.

Hereinafter, the present invention will be explained in detail with reference to the drawings.

Figure 2:
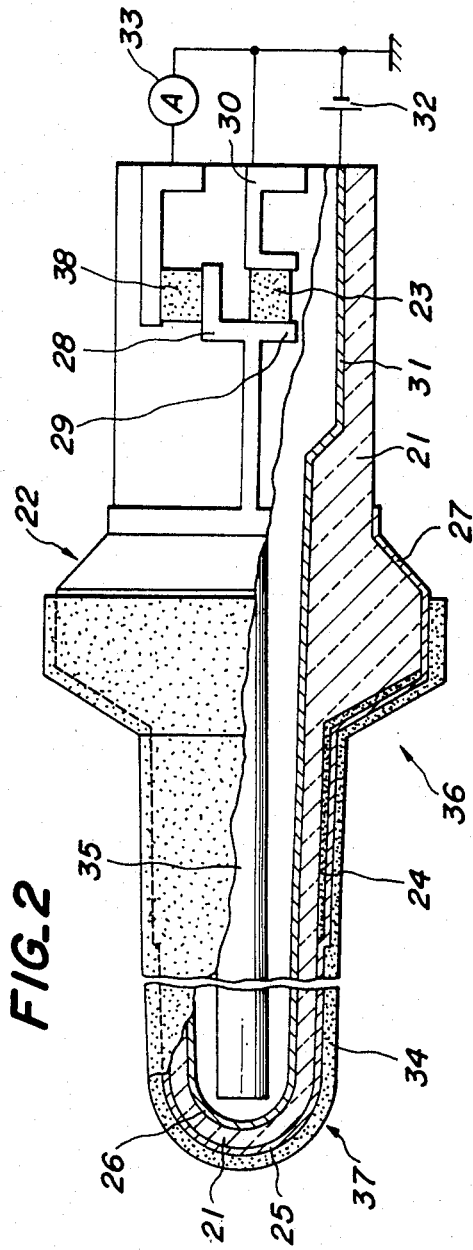
FIG. 2 is a partial cross sectional view showing one embodiment of the electrochemical apparatus according to the invention together with the external circuit.

FIG. 2 shows one embodiment of an oxygen sensor as the electrochemical apparatus according to the invention. In FIG. 2, a solid-electrolyte 21 made of zirconia porcelain has a cylindrical shape with a closed bottom, an opening which faces the air, and has a flange portion 22 at a center peripheral portion in its longitudinal direction. Cermet thick-film resistors 23, 38 made of mainly platinum and alumina and having a predetermined dimension are formed integrally as a variable resistor by a burning at predetermined positions in the opening of the solid-electrolyte 21. An insulation layer 24 made of spinel is formed at the bottom portion of the solid-electrolyte 21 in the manner that an outer surface of the solid-electrolyte 21 is covered along a predetermined length. Further, porous outer electrode 25 and inner electrode 26, both made of platinum, are arranged respectively at an outer surface and an inner surface of the bottom portion of the solid-electrolyte 21. Platinum lead porions 27 and 31 for carrying an external current are arranged in contact with the outer electrode 25 and the inner electrode 26, and extend to the opening portion along the outer surface and the inner surface of the solid-electrolyte 21, respectively.

Moreover, the platinum lead portion 27 connected to the outer electrode 25 is branched into platinum lead portions 28 and 29 as the branch conductor, and the lead portion 29 is connected through the thick-film resistor 23 to a platinum lead portion 30 for use in a connection with an external D.C. power source 32. Further, the platinum lead portion 28 is connected to the D.C. power source 32 through the thick-film resistor 38 and an ammeter 33, and the platinum lead portion 31 extending along the inner electrode 26 is also connected to the D.C. power source 32. These platinum lead portions 27, 28, 29, 30 and 31 are integrally formed on the solid-electrolyte 21.

Further, a ceramic porous layer 34 made of spinel and having a predetermined thickness is arranged as the diffusion means on the outer surface of the bottom portion of the solid-electrolyte 21 in such a manner that the outer electrode 25 is covered. Therefore, in the electrochemical cell constructed by the solid-electrolyte 21, the outer electrode 25, the inner electrode 26 and the ceramic porous layer 34, the gas to be measured (the component to be measured) which is present outside of the bottom portion is diffused through the ceramic porous layer 34 having a diffusion resistance, and is brought into contact with the outer electrode 25. Further, a normal ceramic heater 35 is arranged in the bottom portion of the solid-electrolyte 21 so as to heat the bottom portion of the solid-electrolyte 21 as the electrochemical cell to a predetermined temperature.

When ten electrochemical apparatus 36 are manufactured, a bottom portion of which is inserted into a gas consisting of 7.5% of oxygen and 92.5% of nitrogen and having a temperature of 300° C.; and electrochemical cell portion 37 is heated by the ceramic heater 35 having an output of 40 W; and a D.C. voltage of 0.7 V is applied to the inner electrode 26 (the lead portion 31) as a plus terminal and to the outer electrode 25 (the lead portion 28) as a minus terminal by means of the D.C. power source 32, the current flowing through respective elctrochemical cells 37 greatly vary within a range of 12.5±3.2 mA.

Then, as shown in FIG. 2, the D.C. power source 32 is connected to the inner electrode 26 through the lead portion 31 and is connected to the outer electrode 25 through the lead portion 30. That is to say, the outer electrode 25 is connected to the D.C. power source 32 through the thick-film resistor 23 having a resistance of 7-13Ω and the thick-film resistor 38 having a resistance of 14-26Ω. Further, the ammeter 33 having an inner resistance of 10Ω is connected between the thick-film resistor 38 and the lead portion 30. In this case, the thick-film resistor 23 is trimmed by sandblasting until the ammeter 33 shows 4.5 mA, so that the thick-film resistor 23 is adjusted to generate the output current of 4.62±0.14 mA. By this adjustment, a variation of the output current shown by the ammeter 33 between respective electrochemical apparatus 36 can be made to be small.

Figure 3:
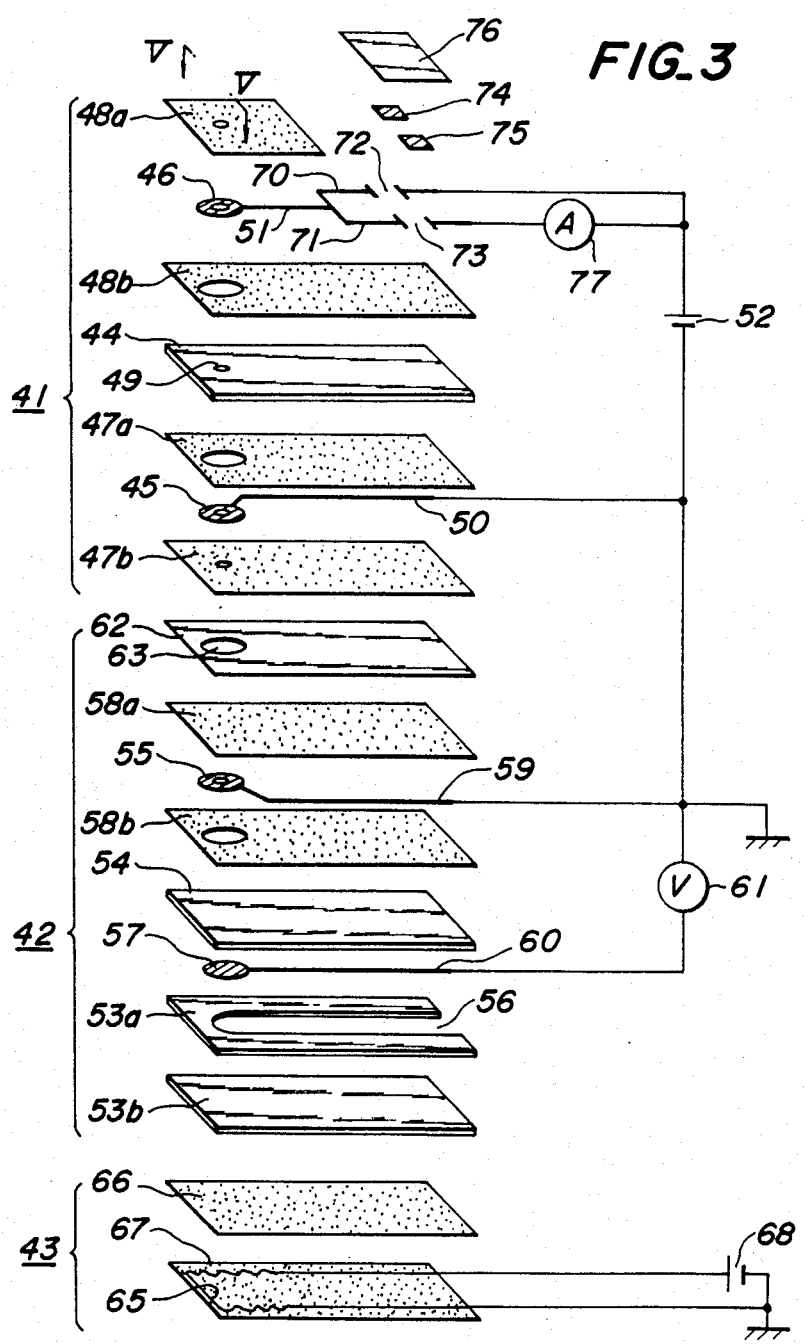
FIG. 3 is an exploded perspective view illustrating one embodiment of the electrochemical apparatus according to the invention together with the external circuit.

FIGS. 3 and 4 are an exploded perspective view and a cross sectional view respectively showing one embodiment of the electrochemical apparatus as an oxygen sensor according to the invention. The oxygen sensor shown in FIGS. 3 and 4 is formed by superimposing an electrochemical pump cell 41, an electrochemical sensor cell 42 and a ceramic heater layer 43 one by one and by burning them integrally.

In this case, the electrochemical pump cell 41 comprises a cell substrate 44 made of a plate-like solid-electrolyte such as a zirconia porcelain with yttria, and an inner pump electrode 45 and an outer pump electrode 46 arranged on both surfaces of the cell substrate 44. Further, in order to protect the pump electrodes 45 and 46 from the gas to be measured or to insulate electrode lead portions 50 and 51 from the cell substrate 44, the inner pump electrode 45 and the electrode lead portion 50 are arranged between porous insulation layers 47a and 47b each made of alumina etc., and the outer pump electrode 46 and the electrode lead portion 51 are also arranged between porous insulation layers 48a and 48b each made of alumina etc.

Further in this embodiment, a gas inlet hole 49 having a size that a diffusion resistance thereof can be ignored substantially, is penetrated through the porous insulation layer 48a, the cell substrate 44 and the porous insulation layer 47b. Moreover, the inner pump electrode 45 and the outer pump electrode 46 of the electrochemical pump cell 41 are connected to an external D.C. power source 52 through the lead portions 50 and 51 respectively, and oxygen ions move from the inner pump electrode 45 to the outer pump electrode 46 through the cell substrate 44 or vice versa corresponding to a direction of current flow between the electrodes 45 and 46.

Contrary to this, in the electrochemical sensor cell 42, a cell substrate 54 and air passage forming members 53a, 53b made of solid-electrolyte such as a zirconia porcelain with yttria as is the same as the cell substrate 44 are superimposed with each other, and a measurement electrode 55 is arranged on the cell substrate 54. Moreover, a reference electrode 57 is arranged on a surface of the cell substrate 54 opposed to the measurement electrode 55, so that the reference electrode 57 is exposed to an air passage 56 formed by the air passage forming members 53a, 53b. In this case, the air passage 56 is formed by surrounding a cut-out portion of the air passage forming member 53a by means of the cell substrate 54 and the air passage forming member 53b, and an opening end portion thereof communicates with the atmosphere.

Further, the measurement electrode 55 is sandwiched between porous insulation thin layers 58a and 58b so as to protect it from the gas to be measured and to insulate a lead portion 59 from the cell substrate 54. Then, an electromotive force generated between the electrodes 55 and 57 due to a variation in oxygen concentration of the atmosphere to which the measurement electrode 55 and the reference electrode 57 are exposed is outputted through the lead portions 59 and 60, and is measured by an external voltmeter 61.

Moreover, an airtight layer 62 made of, for example, zirconia with yttria and having a thin thickness is superimposed between the porous insulation layer 47b of the electrochemical pump cell 41 and the porous insulation thin layer 58a of the electrochemical sensor cell 42, and a cut-out portion is arranged in the airtight layer 62, so that a circular planar space 63 having a thin thickness is formed between the porous insulation layers 47a and 58a as shown in FIG. 4. Further, the gas inlet hole 49 of the pump cell 41 is conducted to a center of the planar space 63, and thus the gas to be measured which is introduced from the gas inlet hole 49 is diffused into the planar space 63.

In this case, the measurement electrode 55 of the sensor cell 42 is brought into contact with the atmosphere in the planar space 63 through the porous insulation layer 58a, and also the pump electrode 45 of the pump cell 41 is brought into contact with the atmosphere in the planar space 63 through the porous insulation layer 47b. It should be noted that the diffusion resistance of the porous insulation layers 58a and 47b are sufficiently smaller than that of the planar space 63, and thus the diffusion resistance of the planar space 63 rules the diffusion of the gas to be measured.

Further, the ceramic heater layer 43 is integrally formed on a surface of the air passage forming member 53b opposed to the air passage 56. The ceramic heater layer 43 is formed by sandwiching a heater constructed by a heating portion and a lead portion between insulation ceramic layers 66 and 67, and is heated by supplying a voltage from an external power source 68 through the lead portions. In this case, the oxygen sensor as the electrochemical apparatus can be operated even in case that the temperature of the gas to be measured is low, because the solid-electrolyte of respective cells 41, 42 and the electrodes thereof can be suitably heated to the operative temperature by the ceramic heater layer 43.

In the electrochemical pump cell 41, the lead portion 51 for connecting the pump electrode 46 to the external DC power source 52, is divided into a first lead portion 70 and a second lead portion 71. The first and second lead portions 70 and 71 are respectively arranged on the porous insulation layer 48b, and further discontinuous portions 72 and 73 are formed in the first and second lead portions 70 and 71, respectively. Further, thick-film resistors 74 and 75 made mainly of ruthenium tetroxide are arranged on the discontinuous portions 72 and 73 respectively, so as to electrically conduct the first and second lead portions 70 and 71. Moreover, in order to protect the thick-film resistors 74 and 75, an overcoat layer 76 made of a suitable ceramic material is formed on the thick-film resistors 74 and 75. Furthermore, both of the first and second lead portions 70 and 71 are connected to the external DC power source, and an ammeter 77 having an inner resistance of 10Ω is further arranged in the second lead portion 71 so as to obtain the pumping current of the electrochemical pump cell 41 as the output current.

Hereinafter, a method of manufacturing the electrochemical element used in the electrochemical apparatus will be explained.

At first, the porous insulation layers 47a, 48b made of alumina, the electrodes 45, 46 and the lead portions 50, 51, 70, 71 both made of porous platinum-zirconia cermet and the porous insulation layers 47b, 48a are successively formed by screen printing on the solid-electrolyte green sheet 44 made of plate-like zirconia having a hole consisting of the gas inlet hole 49. Then, the porous insulation layer 58b, the electrode 55, the lead portion 59, the porous insulation layer 58a and the airtight layer 62 are successively formed by the screen printing on the plate-like zirconia green sheet 54, and the electrode 57 and the lead portion 60 are formed on an opposite surface of the zirconia green sheet 54 in the same manner. Further, the ceramic heater layer 43 is formed by screen printing on the plate-like zirconia green sheet 53b.

Then, three green sheets 44, 53b, 54 and the zirconia green sheet 53a having the cut-out portion as the air passage 46 are laminated by heat, and are burned in the atmosphere at a temperature of 1,400° C. to obtain an integral product. After that, in order to conduct electrically the discontinuous portions 72 and 73 of the first and second lead portions 70 and 71, the thick-film resistors 74, 75 made mainly of ruthenium oxide are formed by screen printing on the discontinuous portions 72 and 73, and are burned in the atmosphere at a temperature of 850° C. Further, the overcoat glass layer 76 is formed by screen printing on the thick-film resistors 74 and 75, and is burned in the atmosphere at a temperature of 850° C. to obtain the desired electrochemical element.

Fifteen of the thus obtained electrochemical elements are heated in the atmosphere by the heater whose input is 8.0 W, and a current flows through the electrochemical cell (pump cell) 41 to make the electromotive force of the electrochemical cell (sensor cell) 42 0.45 V. In this case, the resistance of the thick-film resistors 74, 75 are in a range of 110–165Ω, and the pumping current supplied from the DC power source 52 is 11.16±2.3 mA. Further, the current flowing through the ammeter 77 is about one half of the pumping current mentioned above.

Under such a condition, by applying a laser trimming operation to the thick-film resistor 74 for connecting the discontinuous portion 72 of the first lead portion 70, so as to vary the resistance of the thick-film resistor 74, it is possible to adjust the output current in a range of 8.5±0.04 mA.

Next, in the embodiments shown in FIGS. 5 and 6, the oxygen sensor which embodies the electrochemical apparatus according to the invention is shown. In these embodiments, an insulation layer 82 made of spinel is formed along a predetermined length in an opening end portion of a solid-electrolyte 81 made of zirconia porcelain and having a cylindrical shape with a bottom portion so as to cover an outer surface of the solid-electrolyte 81 along a predetermined length. Further, porous outer electrodes 83 and inner electrode 84 both made of platinum are arranged respectively on an outer surface and an inner surface of the solid-electrolyte 81, and are connected to lead wires 87 and 88 through metal members 85 and 86, respectively. Moreover, a porous ceramic layer 89 made of spinel and having a predetermined thickness is arranged as a diffusion means to cover the outer electrodes 83. An electrochemical cell 90 comprising the solid-electrolyte 81, the outer electrode 83, the inner electrode 84 and the porous ceramic layer 89 is accommodated in a protective cover 94 comprising a louver 91, a housing 92 and a cap 93, and is fixed by means of insulators 95a, 95b and a spacer spring 96, so that the electrochemical cell 90 is brought into contact with the metal member 85, 86. Moreover, a ceramic heater 97 is inserted into an inner portion of the solid-electrolyte 81, and is fixed by means of an insulator 95c and a stopper 98. The lead wire 88 is divided into two branch lines in the protective cover 94, and the branch lines are connected to thick-film resistors 99, 100 formed on the alumina porcelain plate as first and second resistive means. The lead wire 87 and the thick-film resistor 100 are connected to a DC power source 102 through a connector portion 101, and the thick-film resistor 99 is also connected to the DC power source 102 through the connector portion 101 and an ammeter 103. The current supplied from the DC power source 102 to the electrochemical cell 90 is divided corresponding to a dividing ratio defined by the inner resistance of the ammeter 103 and the thick-film resistors 99, 100, and only one of them is measured by the ammeter 103.

Then, the electrochemical cell is temporarily constructed, as shown in FIG. 5, by using a supporting member not shown, and the trimming operation for the thick-film resistor 99 as the first resistive means is effected, while the current flowing through the thick-film resistor 100 as the second resistive means is measured under a predetermined atmosphere and a predetermined temperature so as to obtain the sensor.

Figure 8A:
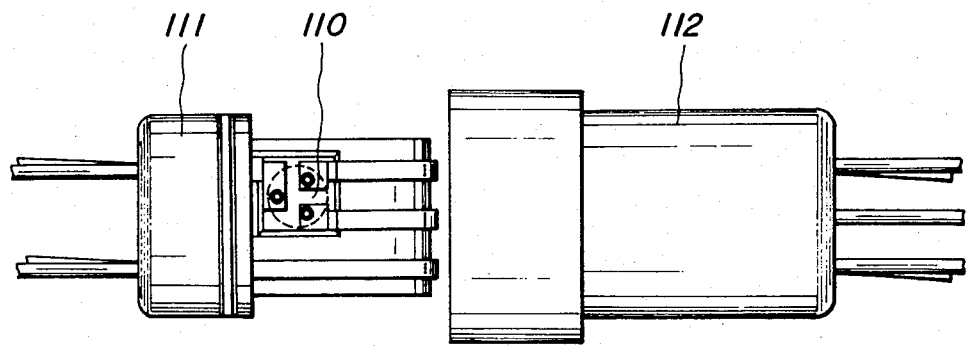
FIGS. 8A and 8B are a plan and a cross sectional view illustrating a connector portion of the embodiment shown in FIG. 7.
Figure 8B:
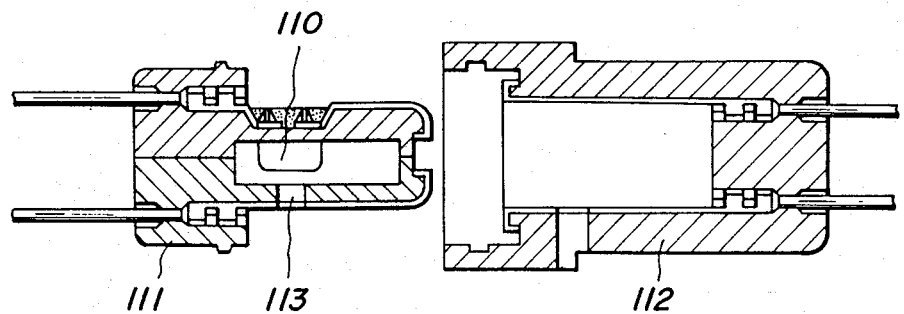

In the embodiments shown in FIGS. 7, 8A and 8B, the first and second resistive means for dividing the pump current are constructed by a potentiometer 110, and the potentiometer 110 is arranged in a connector portion 111 to a side of the electrochemical cell as shown in FIGS. 8A and 8B by a plan view and a cross sectional view thereof. As is the same as the embodiment mentioned above, a resistance ratio of the potentiometer 110 is subjected so as to make constant an output current in air under a predetermined temperature. This adjustment is performed by rotating a screw of the potentiometer with, for example, a screwdriver inserted through a hole 113 for resistor adjustment as shown in FIG. 8B. The connector portion 111 of the electrochemical cell side is connected to a connector 112 of the power source side to perform a measurement operation and a control operation.

Figure 9:
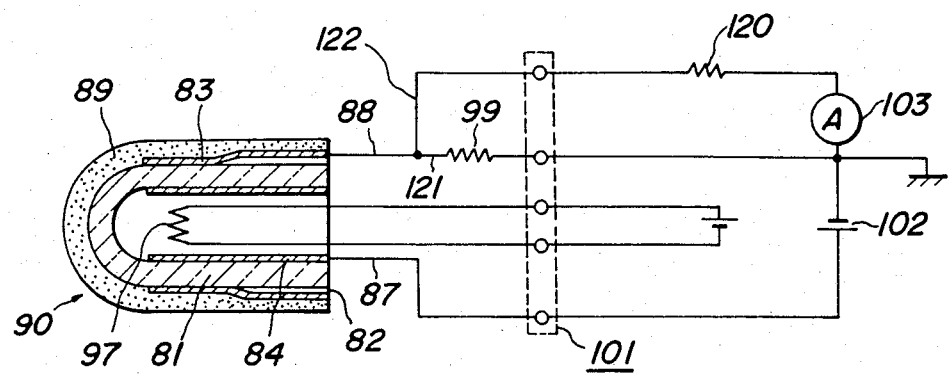
FIG. 9 is a schematic view depicting still another embodiment of the electrochemical apparatus according to the invention together with the external circuit.
Figure 10:
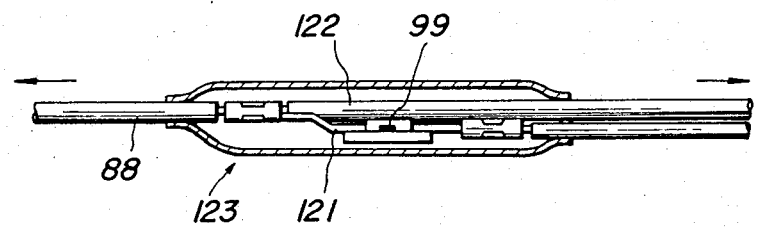
FIG. 10 is a schematic view showing one embodiment of a resistor and a branch line of the embodiment illustrated in FIG. 9.

In the embodiments shown in FIGS. 9 and 10, the thick-film resistor 99 formed on the alumina porcelain plate as the first resistive means is connected between the electrochemical cell 90 and the connector portion 101, and a resistor 120, as the second resistive means is arranged on the power source side with respect to the connector portion 101. In this case, the pump current flowing between the outer electrode 83 and the inner electrode 84 of the electrochemical cell 90 is divided corresponding to a dividing ratio defined by the thick-film resistor 99, the resistor 120 and the inner resistance of the ammeter 103, and only one of them is measured by the ammeter 103. After the thick-film resistor 99 is trimmed in the manner mentioned above, the thick-film resistor 99 is accommodated in a protective cover 123 together with the lead wire 88 and a junction between branch lead wires 121 and 122. In the construction mentioned above such that the resistor 120 as the second resistor is arranged to the power source side with respect to the connector portion 101, it is possible to substitute the resistor 120 for the inner resistance of the ammeter 103.

In the embodiments shown in FIGS. 11 and 12, the first and second resistive means are constructed by the thick-film resistors formed on the alumina porcelain plates, and the resistance of a resistor 132 used for the second resistive means is set to $10.0_{-0.1}^{+0.1}\Omega$. As for a resistor 131 used for the first resistive means, previously trimmed resistors corresponding to thirty standard resistances ranging from $10.0_{-0.1}^{+0.1}\Omega$ to $39.0_{-0.1}^{+0.1}\Omega$ were prepared, and use was made of the most suitable resistor among them for applying the most suitable current dividing ratio with respect to the pump current of the electrochemical cell measured in the atmosphere of 20% oxygen diluted by nitrogen at a temperature of 700° C. The thus selected resistors 131 and 132 were arranged between the electrochemical cell 90 and the connector portion 101, and were accommodated in a protective cover 138 together with the lead wire 88 and a junction between branch lead wires 136 and 137. In this case, the current dividing ratio of the pump current is defined by the thick-film resistors 131, 132 and resistors 133, 134 arranged on the side of the power source 102 with respect to the connector portion 101, and the output current is measured by a voltmeter 135 as a voltage applied to the resistor 133.

Figure 13:
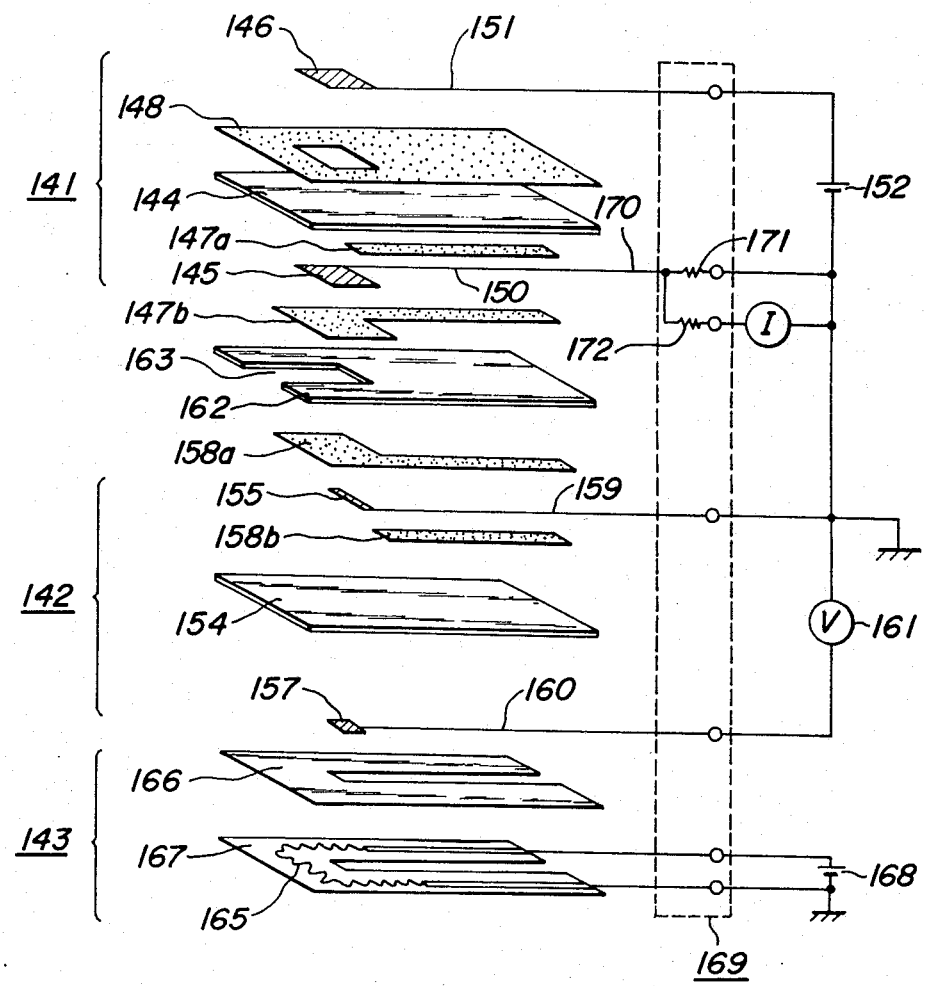
FIG. 13 is an exploded perspective view depicting still another embodiment of the electrochemical apparatus according to the invention.

FIGS. 13 and 14 are an exploded perspective view and a cross sectional view, respectively, showing one embodiment of the electrochemical apparatus as an oxygen sensor including a connector portion 169 according to the invention. The oxygen sensor shown in FIGS. 13 and 14 is formed by superimposing an electrochemical pump cell 141, an electrochemical sensor cell 142 and a ceramic heater layer 143 one by one and by burning them integrally.

In this case, the electrochemical pump cell 141 comprises a cell substrate 144 made of a plate-like solid-electrolyte such as a zirconia porcelain with yttria, and an inner pump electrode 145 and an outer pump electrode 146 arranged on both surfaces of the cell substrate 144. Further, in order to protect the pump electrodes 145 from the gas to be measured or to insulate electrode lead portions 150 and 151 from the cell substrate 144, the inner pump electrode 145 and the electrode lead portion 150 are arranged between porous insulation layers 147a and 147b each made of alumina, etc., and the outer pump electrode lead portion 151 are also arranged on porous insulation layer 148 made of alumina etc.

Moreover, the inner pump electrode 145 and the outer pump electrode 146 of the electrochemical pump cell 141 are connected to an external D.C. power source 152 through the lead portions 150 and 151 respectively, and oxygen ions move from the inner pump electrode 145 to the outer pump electrode 146 through the cell substrate 144 or vice versa corresponding to a direction of current flow between the electrodes 145 and 146.

Contrary to this, in the electrochemical sensor cell 142, on a cell substrate 154 made of solid-electrolyte such as a zirconia porcelain with yttria as is the same as the cell substrate 144 is arranged a measurement electrode 155. Moreover, a reference electrode 157 exposed in the gas to be measured is arranged on a surface of the cell substrate 154 opposed to the measurement electrode 155.

Further, the measurement electrode 155 is sandwiched between porous insulation thin layers 158a and 158b so as to protect it from the gas to be measured and to insulate a lead portion 159 from the cell substrate 154. Then, an electromotive force generated between the electrodes 155 and 157 due to a variation in oxygen concentration of the atmosphere to which the measurement electrode 155 and the reference electrode 157 are exposed is outputted through the lead portions 159 and 160, and is measured by an external voltmeter 161.

Moreover, an airtight layer 162 made of for example zirconia with yttria and having a thin thickness is superimposed between the porous insulation layer 147b of the electrochemical pump cell 141 and the porous insulation thin layer 158a of the electrochemical sensor cell 142, and a cut-out portion is arranged in the airtight layer 162, so that a planar space 163 communicating with the gas to be measured at a tip portion of the cell is formed and thus the gas to be measured is diffused into planar space 163.

In this case, the measurement electrode 155 of the sensor cell 142 is brought into contact with the atmosphere in the planar space 163 through the porous insulation layer 158a, and also the pump electrode 145 of the pump cell 141 is brought into contact with the atmosphere in the planar space 163 through the porous insulation layer 147b. It should be noted that the diffusion resistance of the porous insulation layers 158a and 147b are sufficiently smaller than that of the planar space 163, and thus the diffusion resistance of the planar space 163 controls the diffusion of the gas to be measured with respect to the electrode 145 of the pump cell 141.

Further, the ceramic heater layer 143 is integrally formed on a surface of the sensor cell 142 on the side of the reference electrode 157. The ceramic heater layer 143 is formed by sandwiching a heater constructed by a heating portion and a lead portion between insulating ceramic layers 166 and 167, and is heated by supplying a voltage from an external power source 168 through the lead portions. In this case, the oxygen sensor as the electrochemical apparatus can be operated even in the instance where the temperature of the gas to be measured is low, because the solid-electrolyte of respective cells 141, 142 and the electrodes thereof can be suitably heated to an operating temperature by the ceramic heater layer 143.

In the electrochemical pump cell 141 used in the oxygen sensor according to the invention, a lead wire 170 connected to the lead portion 150 is connected to thick-film resistors 171, 172 formed on the same alumina porcelain plate 173 in a lead portion 169 so as to connect the inner pump electrode 145 to the external DC power source 152. Then, the thick-film resistor 171 is trimmed, and the alumina porcelain plate 173 is molded by a resin to form a cell connector portion 174.

As mentioned above, according to the invention, even if the pumping current of the electrochemical cell consisting of the electrochemical apparatus is varied for every cell, the output of the electrochemical cell can be adjusted precisely and it is not necessary to adjust the external circuit every time the sensor is exchanged, so that the detection accuracy can be advantageously improved. Therefore, it is possible to manufacture the electrochemical apparatus having a constant quality and an extremely small variation of output in a large scale manufacturing operation.

Moreover, the electrochemical apparatus according to the invention can be preferably used for an exhaust gas sensor for an automobile engine operated under a lean atmosphere or a rich atmosphere, and can be applied to the sensor for measuring the gas to be measured such as the exhaust gas burned under a theoretical burning ratio. Further, the electrochemical apparatus according to the invention can also be applied to a detector or a controller for detecting the component related to nitrogen, carbon dioxide, hydrogen other than the oxygen in the gas, and can be also applied to a humidity sensor utilizing a proton conductor.

What is claimed is:

1. An electrochemical apparatus utilizing an electrochemical cell having a solid-electrolyte and at least one pair of porous electrodes arranged in contact with said solid-electrolyte, wherein one of said pair of electrodes is exposed through a diffusion means having a diffusion resistance to a gas to be measured to a space in which the gas to be measured is present, and an atmosphere near said one of the electrode is controlled by an electrode reaction due to a current flowing through said one pair of electrodes, comprising:
    a first branch conductor and a second branch conductor formed by dividing one of conductors respectively connected to said electrodes and arranged connectably to an external power source;
    at least one first resistive means formed in said first branch conductor, a resistive value of which can be arbitrarily adjusted; and
    at least one second resistive means formed in said second branch conductor; whereby a predetermined current corresponding to a predetermined concentration of the gas to be measured flows through one of said first or second resistive means.

2. An electrochemical apparatus according to claim 1, further comprising a current measurement means for measuring the current flowing through one of said first resistive means and second resistive means, whereby an output of said current measurement means is used for a detection of gas concentration of the gas to be measured.

3. An electrochemical apparatus according to claim 1, further comprising a current measurement means connected in series to one of said first resistive means and second resistive means, whereby an output of said current measurement means is used for detecting gas concentration of the gas to be measured.

4. An electrochemical apparatus according to claim 1, wherein said first resistive means and said second resistive means are integrally formed on said solid electrolyte.

5. An electrochemical apparatus according to claim 1, wherein temperature coefficients of respective first resistive means and second resistive means are substantially equal to each other.

6. An electrochemical apparatus according to claim 1, further comprising a second solid-electrolyte and a second electrochemical cell having a pair of porous electrodes and arranged in contact with said second solid-electrolyte, such that one of said pair of electrodes is exposed through said diffusion means to a space in which the gas to be measured is present.

7. A method of manufacturing an electrochemical apparatus utilizing an electrochemical cell having a solid-electrolyte and at least one pair of porous electrodes arranged in contact with said solid-electrolyte, wherein one of said pair of electrodes is exposed through a diffusion means having a diffusion resistance to a gas to be measured in a space in which the gas to be measured is existent, and an atmosphere near said one of the electrodes is controlled by an electrode reaction due to a current flowing through said one pair of electrodes, comprising the steps of:
    forming a first branch conductor and a second branch conductor by dividing one of conductors respectively connected to said electrodes;
    forming at least one first resistive means in said first branch conductor, a resistive value of which can be arbitrarily adjusted;
    forming at least one second resistive means in said second branch conductor; and
    adjusting the resistive value of said first resistive means to a predetermined value so as to obtain a predetermined output in response to a component concentration of the gas to be measured from a current through one of said first branch conductor and second branch conductor.

8. A method of manufacturing the electrochemical cell according to claim 7, wherein said first resistive means and said second resistive means are integrally formed on said solid-electrolyte.

9. A method of manufacturing the electrochemical cell according to claim 7, wherein temperature coefficients of respective first resistive means and second resistive means are substantially equal to each other.

10. An electrochemical apparatus including a connector portion for use in connection with an external power source and an electrochemical cell having a solid-electrolyte arranged in contact with said solid-electrolyte, wherein one of said pair of electrodes is exposed through a diffusion means having a diffusion resistnce with respect to a gas to be measured to a space in which the gas to be measured is existent, and an atmosphere near said one of the electrodes is controlled by an electrode reaction due to a current flowing through said one pair of electrodes, comprising:
    a first branch conductor and a second branch conductor formed by dividing one of conductors respectively connected to said electrodes and arranged connectably to the external power source through said connector portion;
    at least one first resistive means arranged between said electrochemical cell and said connector portion, a resistive value of which can be arbitrarily adjusted; and
    at least one second resistive means formed in said second branch conductor, whereby a predetermined current corresponding to a predetermined concentration of the gas to be measured flows through one of said first or second resistive means.

11. An electrochemical apparatus according to claim 10, wherein both said first resistive means and said second resistive means are arranged between said electrochemical cell and said connector portion.

12. An electrochemical apparatus according to claim 10, wherein said a portion of the resistive means and the branch conductor arranged between said electrochemical cell and said connector portion are arranged in a protective cover of said electrochemical cell.

13. An electrochemical apparatus according to claim 10, wherein a portion of the resistive means and the branch conductor arranged between said electrochemical cell and said connector portion are arranged in said connector cell.

14. An electrochemical apparatus according to claim 10, wherein a portion of the resistive means and branch conductor arranged between said electrochemical cell and said connector portion are arranged in a connection line between said electrochemical cell and said connector portion.

* * * * *